(12) United States Patent
Sandstrom

(10) Patent No.: US 6,926,659 B1
(45) Date of Patent: *Aug. 9, 2005

(54) MAGNETIC FIELD ENHANCEMENT OF TUMOR TREATMENT

(75) Inventor: Robert E. Sandstrom, 49 View Ridge La., Longview, WA (US) 98632

(73) Assignee: Robert E. Sandstrom, Longview, WA (US)

(*) Notice: Subject to any disclaimer, the term of this patent is extended or adjusted under 35 U.S.C. 154(b) by 56 days.

This patent is subject to a terminal disclaimer.

(21) Appl. No.: 10/760,646

(22) Filed: Jan. 20, 2004

Related U.S. Application Data

(63) Continuation of application No. 10/268,300, filed on Oct. 9, 2002, now Pat. No. 6,679,827.
(60) Provisional application No. 60/349,270, filed on Jan. 18, 2002, and provisional application No. 60/328,085, filed on Oct. 11, 2001.

(51) Int. Cl.[7] .............................. A61N 2/04; A61B 17/52
(52) U.S. Cl. ........................................................ 600/9
(58) Field of Search ............................ 600/2, 3, 9–15; 128/897, 898

(56) References Cited

U.S. PATENT DOCUMENTS

| | | | | |
|---|---|---|---|---|
| 6,200,547 B1 | * | 3/2001 | Volkonsky et al. | 424/9.36 |
| 6,482,436 B1 | * | 11/2002 | Volkonsky et al. | 424/489 |
| 6,488,615 B1 | * | 12/2002 | Mitchiner et al. | 600/9 |
| 6,679,827 B2 | * | 1/2004 | Sandstrom | 600/9 |

* cited by examiner

*Primary Examiner*—Samuel G. Gilbert
(74) *Attorney, Agent, or Firm*—Law Office of Timothy E. Siegel; Timothy E. Siegel

(57) ABSTRACT

A method of treating a tumor, comprising creating an elevated concentration of free radicals in said tumor and creating a magnetic field that traverses said tumor and that inhibits the recombination of said free radicals in said tumor, thereby increasing the rate of apoptosis of cancerous cells. A magnetic field of 0.1 mTesla to 10 mTesla is generally used for this purpose.

16 Claims, 1 Drawing Sheet

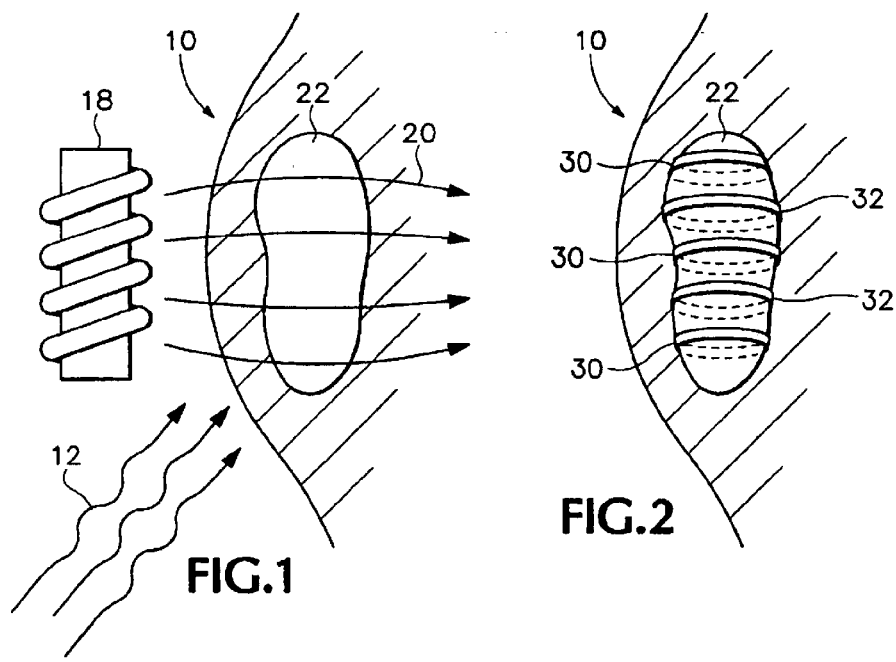
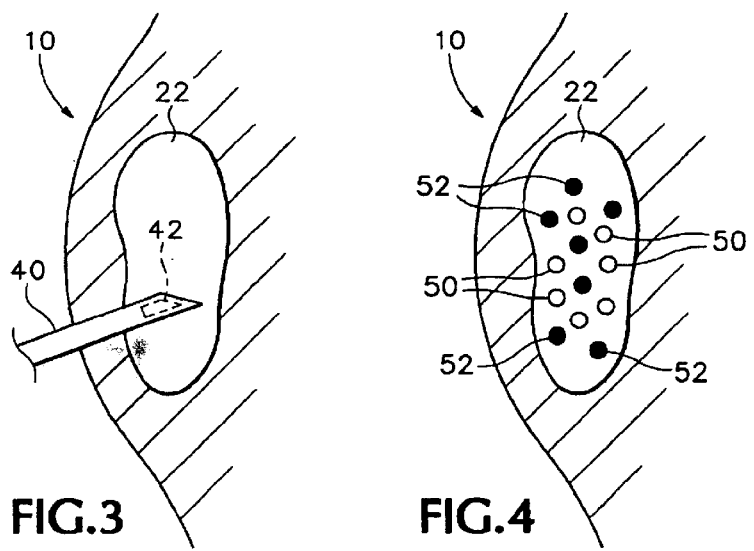

MAGNETIC FIELD ENHANCEMENT OF TUMOR TREATMENT

RELATED APPLICATIONS

This application is continuation of Ser. No. 10/268,300 Oct. 9, 2002 U.S. Pat. No. 6,679,827 which claims the benefit of application Ser. No. 60/328,085 filed Oct. 11, 2001, which claims priority from provisional application 60/349,270 filed Jan. 18, 2002.

BACKGROUND OF THE INVENTION

A central problem in cancer treatment is that of preserving healthy tissue while destroying cancerous tissue. Although radiation therapy generally involves the focusing of radiation on a tumor, at least some healthy tissue generally is located in the irradiated field. This healthy tissue is exposed to and to some degree damaged by the radiation. In chemotherapy healthy tissue is exposed to the chemotherapy agent and may be damaged.

Moreover, research has shown that much of the effect of radiation therapy and a substantial component of some approaches to chemotherapy are mediated by free radical effects in tumor tissue. The mechanisms whereby free radicals produce tumor cell death include direct enzymatic effects, DNA damage and induction of apoptotic pathways.

Our understanding of the physics and chemistry of free radicals and paired radicals has gradually increased over the past ten years. A free radical is any chemical species capable of an independent existence that has an unpaired electron in its valence shell. The presence of an unpaired electron in the valence shell causes free radicals to be paramagnetic and exhibit magnetic properties when exposed to a magnetic field.

Free radicals may be formed by any of several mechanisms including but not limited to:

Ultraviolet induced homolytic fission as may be encountered in laser ablation therapy of tumors;

Specific chemical reactions as encountered with pharmacological chemotherapy e.g. bleomycin;

Ionizing radiation as the result of external beam irradiation, antibody directed or site selective radionucleotide administration or through implantation radiotherapy e.g. prostatic brachyotherapy;

Thermal induction as in hyperthermic therapy; or Ultrasound induced acoustic cavitation.

Free radicals once generated may recombine. The biologic effects of free radicals in tissue are determined by the net reactive fraction namely the "escape" population that does not recombine rapidly. Factors, which influence pair recombination, include the viscosity of the reaction environment, temperature, bystander effects and the quantum state of the free radical. The quantum state of the free radical is defined by the applicable Schrodinger equation (HΨ=EΨ) where H is a Hamiltonian operator and Ψ are sets of wave functions (Eigenfunctions). The Eigenfunctions are defined by a set of four quantum numbers: n-the principal quantum number, 1-the orbital quantum number, $M_l$-the magnetic quantum number and $M_s$-the spin quantum number. Of particular significance to this discussion is the spin quantum number.

The spin quantum number for an unpaired orbital electron can assume one of two values either $+\frac{1}{2}$ or $-\frac{1}{2}$. The wave distribution function determined by spin quantitization is a vector quantity and subject to influence by a superimposed magnetic field. When two electrons share an orbital space they must have opposite spin polarity. This phenomenon is dictated by the Pauli Exclusion Principal that postulates that no two electrons can occupy the same quantum state.

Spin polarity is conventionally referred to as up spin (↑)+½ or down spin (↓)-½. Shared valence electrons in the formation of chemical bonds also must have opposite spin polarity. When covalent bonds are severed as in the formation of free radicals spin polarity is preserved.

The unpaired electron in the valence orbital of a free radical in a magnetic field will precess in a manner comparable to Larmor precession described for charged particles in classic electrodynamics. Quantum precession leads to spin phase transitions between the singlet state where antiparallel spin vectors apply and triplet states where parallel spin vectors apply. The singlet state is favorable for recombination because antiparallel spin orientation is preserved and a covalent bond can be established. Triplet state configurations are unfavorable for recombination because parallel spin orientation is induced. In a magnetic field there are three triplet state configurations, which are vector quantities that due to precession in the magnetic field are no longer energy equivalent and are said to be nondegenerate.

The strength of the applied magnetic field, which maximizes the spin phase mixing effect, is dependent on the quantum state of the free radical or the system of free radicals. In general optimum phase mixing is achieved at relatively low magnetic field strengths (0.1–10.0 mTesla) within the hyperfine coupling energy levels of the radical pair.

The singlet state ($S_1$) characterized by antiparallel spin vectors will prevail in the absence of a magnetic field when homolytic fission of a covalent bond occurs to form a free radical pair. In the presence of a magnetic field of appropriate strength, the triplet states, $T_{-1}$, $T_0$ and $T_{+1}$ are equally probable energy states and are distinct and nondegenerate. The theoretic distribution between singlet and triplet states will be 25% singlet and 75% triplet. Such a distribution will theoretically increase the effective concentration of escape radicals by 75%. In experimental situations the yield is limited by non-quantum factors including viscosity effects, temperature, diffusion and bystander effects. However, increases in escape radical reactivity of 20–40% are documented in experimental systems where free radical escape reactions are measured.

SUMMARY

The present invention is a method of treating a tumor in which an elevated concentration of free radicals is created in the tumor by one of several methods described. In addition, a magnetic field is created that traverses the tumor and that inhibits the recombination of the free radicals in the tumor enhancing escape radical reactivity, which results in enhanced tumoricidal effect, by increasing the rate of apoptosis of cancerous cells.

The foregoing and other objectives, features and advantages of the invention will be more readily understood upon consideration of the following detailed description of the invention, taken in conjunction with the accompanying drawings.

BRIEF DESCRIPTION OF THE DRAWINGS

FIG. 1 is an illustration of a tumor being treated by radiation therapy augmented by a magnetic field.

FIG. 2 is an illustration of a tumor being treated by strips of implanted radioactive material interspersed with strips of implanted magnetic material.

FIG. 3 is an illustration of a tumor into which a magnet has been introduced by a laparoscope.

FIG. 4 is an illustration of a tumor that is being treated by a combination of radioactive beads and magnetic beads.

DETAILED DESCRIPTION OF THE PREFERRED EMBODIMENTS

Referring to FIG. 1, in a first preferred embodiment a patient's body 10 is subjected to radiation 12 that travels through the body 10 in a first direction. A magnet 18 is oriented so as to create a magnetic field 20 in the vicinity of a tumor 22 of one milli Tesla (mT). The magnet 18 is aligned so that the area of intersection of the radiation and the magnetic field conforms to the outline of the tumor. Typically in this operation magnets 18 are electromagnets, as they may be controlled to vary the intensity of the magnetic field over time. In one preferred embodiment, however, static magnets are used as they can be more easily shaped to reflect the cross section of the tumor. The magnetic field may also be induced by magnetite, sprayed or painted magnetic films or implants or any other method of creating a magnetic field. In addition, magnetic shielding may be introduced to block ambient magnetic field effects.

The radiation 12 used may be gamma ray, x-ray or photon radiation. In addition, as used in this application, the term radiation also encompasses sound waves as in ultrasound-induced acoustic cavitation, and radiation 12 may take this form.

Referring to FIG. 2, a tumor 22 may be treated by placing radioactive strips 30 about it. Additionally, magnetic strips 32 are placed to create a magnetic field in the tumor 22.

Referring to FIG. 3, a laparoscope 40 is used to introduce a magnet 42 directly into the tumor. The tumor is then additionally treated with an injection of chemotherapy agents, which could also be from the laparoscope 40 or with radiation as in FIG. 1. Laparoscope 40 may also include a light source, for performing photon source radiation. In one preferred embodiment, laparoscope 40 injects a chemical agent that is activated by light waves to yield free radicals and also includes a light source for activating the chemical agent.

FIG. 4 shows a tumor that is being treated by a set of radioactive beads 50 and a set of magnetic beads 52, adapted to create a magnetic field.

For any of the above-described techniques, the magnetic field created is preferably between about 0.1 mTesla and 10 mTesla (10–1,000 gauss).

In an additional preferred embodiment, substances that form free radical pairs in the presence of radiation (including among other forms, light radiation) are injected into the tumor or into the vicinity of the tumor. In a variant of this embodiment, the substance that is injected forms free radical pairs that are particularly likely to cause apoptosis (cell death). In another variant, the substance that is injected forms free radical pairs that are particularly sensitive to a magnetic field. The free radical pairs produced may be easily induced into the triplet state by way of the application of a low intensity magnetic field.

In tumor treatment systems where the effectors of tumor cell killing are the escape free radicals, analysis indicates that a magnetic field on the order of 0.1 to 1.0 milliTesla will cause a 30–40% increase in tumor lethality. Accordingly, in one preferred variant of a treatment system using radiation mediated free radical production, the equivalent tumoricidal effect is achieved at significantly lower overall radiation levels. In another variant, higher tumoricidal effect is achieved at equivalent radiation levels.

Furthermore, since the magnetic effect is a vector quantity, the magnetic field, in one preferred embodiment, is contoured to fit the topography of an irradiated tumor allowing more focused radiation effect and sparing normal tissues. This topologic modeling complements and improves prior art radiation treatment field design by introducing an independent vector specific variable.

As noted, at least one preferred embodiment makes use of oscillating or alternating magnetic fields to influence radical reactivity. However, the frequency of the oscillating or alternating field will be dependent on the short radical recombination time window. Subtle combinatorial magnetic effects, which combine static and modulated magnetic field effects, may offer advantages in specific situations.

At least one preferred embodiment makes use of modifications of the ambient magnetic field environment to optimize the magnetic effect described. In cases where electronic equipment near to the intended tumor target modifies the electromagnetic environment, shielding is used to prevent ambient electromagnetic interference. In one preferred embodiment, low carbon steel shields are used for this purpose. In another preferred embodiment mumetal shielding is employed.

Radical pair recombination as mentioned will be influenced by the biologic reaction environment and modifications to viscosity, temperature and structural properties including cell membranes and organelles may be exploitable parameters to further enhance the tumoricidal benefit described here.

In a further preferred embodiment, the magnetic field and the substances injected are specifically adapted to destroy specific cell constituents that are targeted by known targeting mechanisms, e.g. antigen-antibody targeting.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method of treating a tumor, comprising:
    (a) creating an elevated concentration of free radicals in said tumor; and
    (b) creating a magnetic field that traverses said tumor and that inhibits the recombination of said free radicals in said tumor, thereby causing an increased rate of apoptosis of cancerous cells.

2. The method of claim 1, wherein said free radicals are created in said tumor by means of electromagnetic radiation.

3. The method of claim 2, wherein said electromagnetic radiation is in the frequency band from $10^{10}$ Hz to $10^{20}$ Hz.

4. The method of claim 2, wherein said electromagnetic radiation is in the frequency band from $2*10^{14}$ to $10^{15}$ Hz.

5. The method of claim 2, wherein said electromagnetic radiation is applied to said tumor in conjunction with the introduction of a chemical agent.

6. The method of claim 1, wherein said free radicals are created in said tumor by means of the introduction of a chemical agent.

7. The method of claim 1, wherein said magnetic field is of a magnitude that facilitates the interstate crossing of singlet state free radical pairs to triplet state free radical pairs.

8. The method of claim 1, wherein said magnetic field has a magnitude in the range of 0.1 Tesla to 10 milli Tesla through said tumor.

9. The method of claim 1, wherein said magnetic field is of a magnitude that inhibits the interstate crossing of triplet state free radical pairs to singlet state free radical pairs.

10. The method of claim 1, wherein said magnetic field is created by at least one magnet positioned exterior to said tumor.

11. The method of claim 1, wherein said magnetic field is created by magnetic particles that are injected into proximity to said tumor.

12. The method of claim 1, wherein said elevated concentration of free radical pairs is created by sound waves.

13. The method of claim 1, wherein said elevated concentration of free radical pairs is created by acoustic cavitation.

14. The method of claim 1, wherein said free radicals interfere with the operation of enzymes within said tumor cells.

15. The method of claim 1, where free radical magnetic effects are contoured, scaled or designed to conform to tumor volume or shape.

16. The method of claim 1, where free radical reactivity is enhanced by introducing electromagnetic shielding to block ambient electromagnetic interference.

* * * * *